United States Patent [19]

Dahl

[11] 4,003,377
[45] Jan. 18, 1977

[54] PATIENT VENTILATOR

[75] Inventor: William R. Dahl, Littleton, Colo.

[73] Assignee: Sandoz, Inc., E. Hanover, N.J.

[22] Filed: Aug. 21, 1975

[21] Appl. No.: 606,644

[52] U.S. Cl. .......................................... 128/145.8
[51] Int. Cl.² ...................................... A61M 16/00
[58] Field of Search ......... 128/145.8, 145.6, 145.5, 128/142, 142.2, 188

[56] References Cited

UNITED STATES PATENTS

| 3,834,382 | 10/1974 | Lederman et al. | 128/145.8 |
| 3,910,270 | 10/1975 | Stewart | 128/188 |
| 3,916,889 | 11/1975 | Russell | 128/145.8 |

Primary Examiner—Robert W. Michell
Assistant Examiner—Henry J. Recla
Attorney, Agent, or Firm—Gerald D. Sharkin; Robert S. Honor; Walter F. Jewell

[57] ABSTRACT

An improved patient ventilator for providing a mode of operation wherein mandatory breaths are supplied to a patient intermittently, and wherein those mandatory breaths are synchronized with the patient's normal breathing cycle. An adjustable timer provides an output signal for controlling the duration between mandatory breaths, and a delay circuit prevents the output signal from the timer from initiating the mandatory breath for a predetermined delay period to permit the patient to initiate that breath himself. The intermittent mandatory breaths are made "mandatory" by closing off an exhalation valve while a fixed quantity or pressure level of oxygen is supplied to the patient.

4 Claims, 3 Drawing Figures

PATIENT VENTILATOR

BACKGROUND OF THE INVENTION

Patient ventilators, that is, devices for controlling or assisting the breathing of a patient, are known in the art, and an embodiment of such a ventilator which is particularly compatible with the improvement disclosed herein is described in U.S. Pat. application Ser. No. 401,739, entitled Patient Ventilator Apparatus, filed on Sept. 28, 1973, in the name of George K. Russell. In that apparatus, a desired oxygen-air mixture is supplied under pressure to a patient, in a specific desired quantity, and in desired inhale/exhale half-cycles. For example, the ventilator apparatus may be controlled by a master flip flop circuit, pneumatically or electrically operated, so that both the inspiratory and expiratory half-cycles can be initiated by manual triggers and by timing circuit triggers, and wherein the inspiratory half-cycle can be triggered also by a detector device which senses an attempt by the patient to inhale, while the expiratory half-cycle can be triggered also by a volume limit sensor and a pressure limit sensor.

In the use of such apparatus for controlling the breathing of patients, it is often necessary to "wean" the patient from dependence upon the apparatus, and for this purpose the apparatus is adjusted so that the number of mandatory breathing cycles applied to the patient are slowly reduced until the patient is able to breath on his own. This concept is referred to as "intermittent mandatory ventilation" (IMV).

In the use of the apparatus in this manner, it is preferable to ensure that each mandatory breath supplied to the patient is initiated when the patient has concluded a voluntary expiratory half-cycle, so that voluntary exhalations of air are not interrupted. This concept will be referred to as synchronized intermittent mandatory ventilation (SIMV), and an object of the instant invention is to provide circuitry for accomplishing this synchronized function.

SUMMARY OF THE INVENTION

In accordance with the present invention a control system is provided for connection to a patient ventilator apparatus, so that the apparatus can be operated to wean a patient from dependence thereon. In particular, the present invention relates to an apparatus which permits the patient to breath voluntarily, but which supplies mandatory breaths to the patient on an intermittent basis until his breathing capacity is self-sufficient. In the present invention the intermittent breaths are provided in a synchronized relationship with respect to the patient's voluntary breathing.

To accomplish this function, there is provided a control switch for permitting normal operation of the ventilator, wherein an exhalation valve is closed during the inspiratory half-cycle so that each breath is mandatory, and for permitting the selection of a synchronized intermittent mandatory ventilation (SIMV) mode when it is desired to wean the patient from dependence on the apparatus.

As mentioned above, the ventilator may be controlled to initiate the inhale/exhale half-cycles by means of a master flip flop circuit, wherein the flip flop may be controlled manually and by timers in both half-cycles, and wherein the inspiratory half-cycle may also be initiated by a patient trigger circuit which detects an attempt by the patient to inhale, while the expiratory half-cycle may also be initiated by a volume limit sensor and a pressure limit sensor. During the SIMV mode, the timing device for timing the inspiratory half-cycle is deactivated, because its timing rate is not matched with the slower rate of the exhalation timer, and the device for timing the expiratory half-cycle is controlled to increase its normal timing period. This increased timing period is adjustably controlled so that the timer can be used to initiate the mandatory breaths which are supplied at a reduced rate from the normal breathing rate, and so that the inspiratory half-cycles are initiated synchronously with the patient's attempts to inhale. That is, the timer for the exhale period provides for mandatory inspiratory half-cycles on an intermittent basis, and in a manner wherein the breathing period is synchronized with the normal breathing period of the patient. Thus, when the extended timing period for the exhalation timer terminates prior to the normal initiation period for an inspiratory half-cycle, the device will automatically delay such initiation for a period of up to four seconds, whereupon if the inhale period has not been initiated by the patient, the device will automatically switch to provide a mandatory breathing inhalation period.

These functions are performed, in one embodiment of the invention, by circuitry including a one-shot circuit for generating a signal at the commencement of the first exhale period after the SIMV mode is selected. The output of the one-shot circuit switches an SIMV flip flop circuit to provide an input signal for an OR/NOR circuit, and the OR output of that OR/NOR circuit deactivates the inspiratory timer. The output of the SIMV flip flop also charges a capacitive device which maintains a pneumatic switch in an open condition while it remains charged. Furthermore, selection of the SIMV mode opens a bypass circuit which normally constitutes a supply path to the exhalation timer, and couples a variable restriction into that supply path so that the timing period is increased. During the SIMV mode the exhalation valve remains open except during the mandatory breathing period, so that the patient can breath normally. When the timing period of the exhalation timer finally "times out", the pneumatic switch controlled by the capacitive device provides a four second delay to permit the patient to voluntarily initiate an inspiratory half-cycle voluntarily. At the end of four seconds, a signal is provided to initiate the inhale half-cycle if such initiation has not already taken place. The output of the exhalation timer is also coupled to the SIMV flip flop and the OR/NOR circuit, to cause the exhalation valve to remain closed during the mandatory breathing period so that a full quantity of oxygen is supplied to the patient.

In another embodiment of this invention, a one-shot circuit, a flip flop circuit, and an OR/NOR circuit are provided to function as described above with respect to the first embodiment, but the SIMV select switch produces two ranges of mandatory breaths per minute. In the higher range, the above-mentioned variable restrictor has a second restrictor coupled in parallel therewith to permit the selection of a high number of breaths per minute; and, in the lower range, the parallel path including the second restrictor is blocked so that the variable restrictor may permit a much lower range of breaths per minute.

BRIEF DESCRIPTION OF THE DRAWINGS

A preferred embodiment of the present invention will be described herein in conjunction with the accompanying drawings. In such drawings.

DETAILED DESCRIPTION OF THE PREFERRED EMBODIMENT

Figure 1:
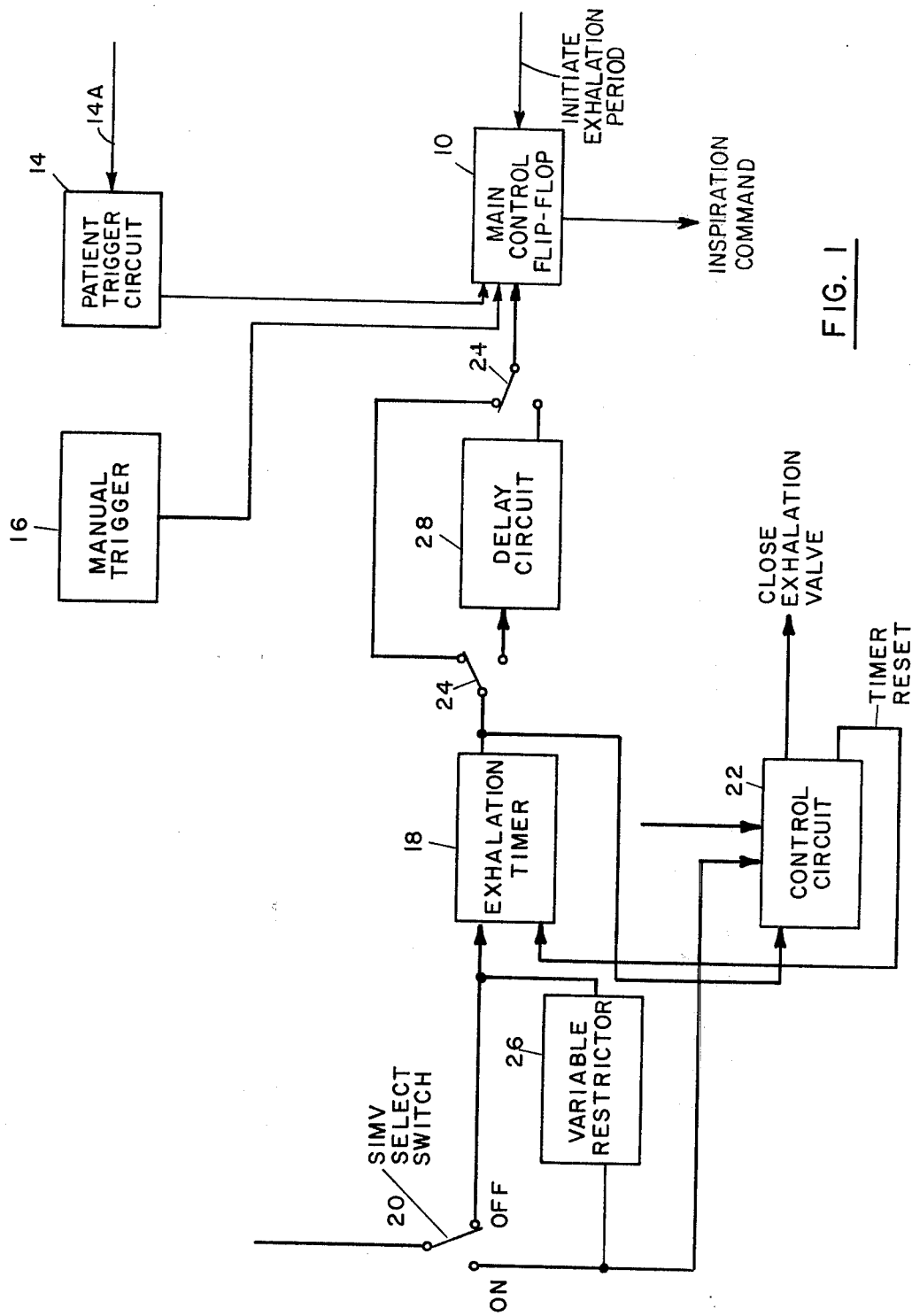
FIG. 1 is a block diagram illustrating the function of the instant invention.

The SIMV concept will be described herein in conjunction with the elements of an existing ventilator apparatus, the details of which are disclosed in U.S. Pat. application Ser. No. 401,739. In a portion of the existing system, as included in the present FIG. 1, a master flip flop 10 is provided with an output 12 which produces command signals for initiating the inspiratory half-cycle of operation for the ventilator. In this regard, an inspiratory command at the output conduit 12 is generated in response to an input received at the left-side of the flip-flop 10, and is terminated when an input is received at the right-side thereof. As illustrated, the flip flop is capable of generating its inspiratory command in response to any one of three signals, which may be received from a patient trigger circuit 14, a manually operated trigger circuit 16, or an exhalation timer 18. The patient trigger circuit is actuated by the pressure in a patient reference line, so that when a pressure exists in that line below a certain reference level, thereby signifying an attempt by the patient to inhale, the patient trigger circuit will generate an output to trigger the flip flop 10 and initiate the inspiratory command. In the normal mode of operation, namely, when an SIMV select switch 20 is in the OFF position, a supply of air is coupled through the switch to the exhalation timer 18 in order to permit the timer to operate whenever there is an absence of a reset signal from a control circuit 22. Also, when the select switch 20 is in the OFF position the control circuit 22 controls a switch 24 to couple the output of the timer 18 directly to the input side of the flip flop. Thus, in the normal mode of operation, and in the absence of a prior signal from the patient trigger circuit 14 and the manual trigger circuit 16, the timer 18 will "time out" and its output will cause the flip flop to immediately generate an inspiratory command. Subsequently, the switch control circuit 22 will couple a reset signal to the exhalation timer as soon as it detects the inspiratory command along conduit 12, so that the timer will be deactivated during the inspiratory period. As described in the above-identified application Ser. No. 401,739, the inspiratory portion of the cycle will continue until a terminating signal is received from, for example, a manually operated trigger, a pressure limit sensing device, an inspiratory timer, or a volume limit device.

When it is desired to wean a patient from dependence upon the ventilator, the SIMV select switch 20 is moved to its ON position to increase the timing out period of the exhalation timer, so that mandatory breaths are applied intermittently according to the increased time period. Furthermore, in the SIMV mode the control circuit 22 operates to de-energize the inspiratory timer since its timing period is not matched to the increased period of the exhalation timer. Specifically, the exhalation timing period is controlled to provide forced breaths at selectable intermittent intervals by varying the timing period for the exhalation timer so that it provides an output at a rate related to the respiratory frequency, and so that the output of the timer causes a "full breath" to be applied to the patient ventilator hose.

In order to increase the timing period for the exhalation timer, the air supplied thereto is reduced by a device 26 which may simply constitute a restriction in the inlet to the timer. Then, in the SIMV mode, when the timer finally times out, an output signal from the switch control circuit 22 controls the switch 24 to apply the output of the timer through a delay circuit 28 to the flip flop 10. The delay circuit 28 delays the actuating signal for a period of four seconds to permit the patient himself to trigger the flip flop in response to his attempt to inhale. On the other hand, if the patient trigger circuit 14 does not detect any such attempt to inhale, then the signal from the exhalation timer 18 finally actuates the flip flop circuit 10 after the 4 second delay.

Figure 2:
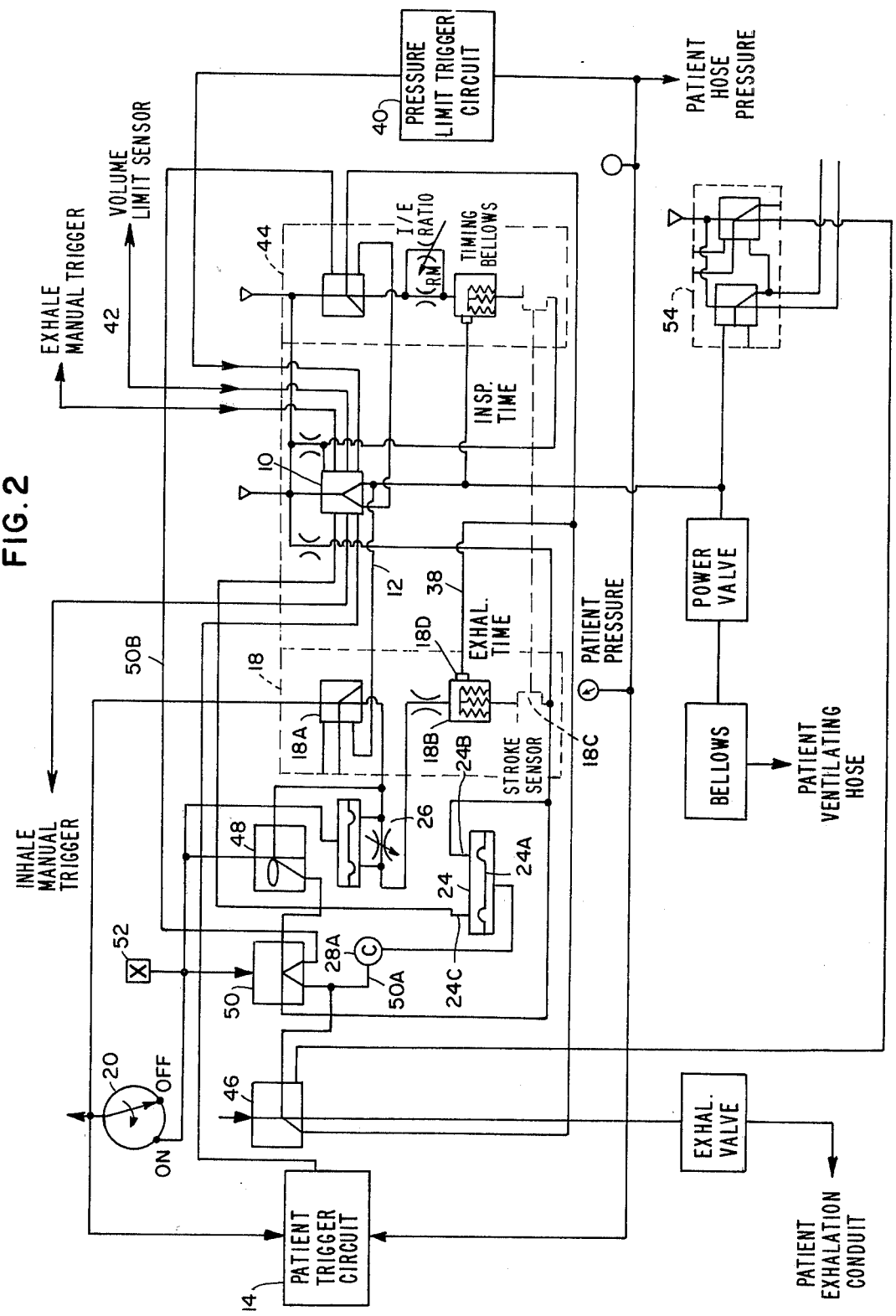
FIG. 2 is a circuit diagram illustrating the specific elements included in a first embodiment of the invention.

Specific elements for accomplishing the above-described functions, in the manner illustrated by the block diagram shown in FIG. 1, are depicted in FIG. 2 of the drawings which is seen to be similar to FIG. 2 of the drawings in the above-mentioned application Ser. No. 401,739. Thus, it is to be understood that one advantage of the instant invention is that it can be combined easily with an existing patient ventilator circuit in order to provide all of the desired functions discussed above.

In the operation of the elements depicted in FIG. 2, a primary mode switch (not shown) is adjusted so that the ventilator circuit will function in an assist/control (A/C) mode, wherein the apparatus will merely assist the patient's breathing attempts, but will automatically control the patient's breathing in the absence of the detection of such voluntary breathing. The SIMV mode is made operable only when the A/C mode has been selected on the primary mode switch, at which time an energizing signal is coupled along a conduit 30, so that the patient trigger circuit 14 is energized to cause an inspiratory half-cycle to be initiated in response to a corresponding attempt of the patient to inhale. In the absence of such an attempt, when the SIMV switch is in the OFF position, the exhalation timer 18 will initiate the inhale portion of the half-cycle. The exhalation timer may constitute, for example, a NOR circuit 18A, a timing bellows 18B and a sensor 18C. The output of the NOR circuit 18A is coupled to the timing bellows 18B through a switch 32 having a flexible diaphragm 34 which closes off two ports 36A, 36B in a sealed chamber of the switch. The port 36A is coupled to the output of the NOR circuit 18A, while the port 36B is coupled to a sealed chamber of the timing bellows 18B. Connected in parallel with the two ports 36A and 36B, externally of the switch 32, is the variable restrictor 26 which is used to slow down the charging time of the bellows 18B, in the SIMV mode, when the diaphragm 34 seals off the ports internally of the switch 32. With this construction, the ports 36A, 36B are maintained in communication during normal operation of the ventilator device, when the selector switch 20 is in the OFF position. Accordingly, under these operating conditions, when there is no signal on the inspiratory command line 12 which is connected as an input to the NOR circuit 18A, an output is produced by the NOR circuit 18A and is shorted through the switch 32 to the bellows element 18B. This causes the bellows element 18B to callapse at a predetermined rate until finally the stroke sensor 18C is closed to send a signal to the master flip flop, through the switch 24, to end the exhalation period. A dump valve 18D is provided on the timing bellows 18B, and when a pressure signal is removed from a conduit 38 connected to that dump valve, the air charged therein through the NOR circuit 18A is completely vented to the atmosphere.

Referring still to the operating condition wherein the SIMV switch 20 is in the OFF position, the patient's breathing is controlled in the manner described in detail in the application Ser. No. 401,739 wherein both half-cycles of the breathing period can be controlled by means of the master flip flop circuit 10 having its inspiratory command output 12 coupled to control a power valve for operating a bellows device which supplies a desired oxygen-air mixture to the patient through a ventilating hose. The supply of air may be continuously provided to the patient until a pressure limit trigger circuit 40 is actuated in response to a predetermined pressure in a conduit thereof coupled to the oxygen supply hose to the patient. Thus, if the pressure of the oxygen-air mixture supplied to the patient exceeds a predetermined level, the pressure limit circuit will generate an output applied to the side of the flip flop which terminates the inhale half-cycle. Also, a volume limit sensor 42 has an input coupled to a signal indicating that a predetermined quantity of oxygen-air mixture has been supplied to the patient, so that if such predetermined volume is reached the master flip flop will be switched to terminate the inhale half-cycle. Furthermore, an inspiratory timer 44 is provided, and corresponds identically to the exhalation timer 18 with the exception that the output thereof is connected directly to an input of the master flip flop so that when the timer indicates a completed inspiratory timed period, the flip flop will terminate such period. Also, the dump valve for the timing bellows of the inspiratory timer is held closed by the inspiratory command output of the master flip flop so that the timer is only operable during the inhale period.

In summary, the master flip flop controls inhale/exhale periods and in turn is controlled by the inputs thereto from the manual triggers, the timers, the pressure and volume trigger circuits, and the patient trigger circuit. Also, when the SIMV switch 20 is in the OFF position a valve in the exhalation conduit is maintained closed during the inspiratory period by means of the output of the NOR output of an OR/NOR circuit 46 since neither of the inputs to that circuit receives a signal during the inhale period. Whenever the exhalation valve is closed, the patient must accept a full volume of oxygen.

Referring now to the elements which relate to the SIMV mode, it is seen that when the switch 20 is moved to its ON position, an energizing signal is applied to the switch 32 so that the diaphragm 34 thereof seals the ports 36A, 36B and couples the variable restrictor 26 into the charging line for the exhalation timing bellows 18B. Furthermore, the signal coupled through the switch 20 is applied to energize a one-shot circuit 48, an SIMV flip flop circuit 50, and an indicator device 52 for indicating the SIMV mode of operation. The input to the one-shot circuit 48 is coupled from the output of the NOR circuit 18A of the exhalation timer so that at the commencement of the first exhalation period after the switch 20 is moved to the ON position, a signal will be applied to the energized one-shot circuit 48. The output of that circuit 48 is coupled as one of the inputs of the SIMV flip flop 50 and causes an output signal to be produced by the flip flop 50, which output signal is coupled along a conduit 50A as one of the inputs of the NOR circuit 46 and as an input to a capacitive device 28A. The other side of the capacitive device is coupled as a control input to the switch 24 having a diaphragm 24A which seals a pair of ports 24B, 24C coupled respectively to the exhalation timer sensor 18C and as an input to the master flip flop 10 for initiating an inspiratory half-cycle. The other input to the SIMV flip flop 50 is coupled to the stroke sensor output 18C of the exhalation timer, while the other output 50B thereof is coupled as a deactuating signal to the inspiratory timer 44.

The OR output of the OR/NOR circuit 46 is also coupled as a deactuating signal to the inspiratory timer 44, and to the dump valve 18D of the exhalation timer. Finally, the second input to the OR/NOR circuit 46 is coupled from the NOR output of a dual OR/NOR circuit 54 having its input connected to the inspiratory command line 12.

As is apparent from the foregoing description of the SIMV elements, the inspiratory timer is disabled at all times when the SIMV mode is selected by positioning the switch 20 in the ON position, and this is accomplished by the signals coupled to the inspiratory timer from the OR output of the OR/NOR circuit 46, which signals are present at all times during the timing period of the inspiratory timer, and by the signals coupled from the output 50B of the SIMV flip flop 50 which output is produced in response to a signal from the stroke sensor 18C. In summary, it can be seen that the inspiratory timer is disabled in response to either output of the SIMV flip flop 50, and one or the other outputs thereof will provide an output signal at all times during the SIMV mode.

Aside from the disabling of the inspiratory timer, the elements will operate the same during the inspiratory half-cycle, and will terminate such half-cycle in the same way, regardless of whether the SIMV switch 20 is positioned in the ON or OFF positions. In the absence of an inspiratory command generated on the output 12 of the master flip flop 10, the NOR circuit 18A of the inspiratory timer will provide a charging flow for the bellows portion 18D thereof through the restrictor 26 since the ports 36A and 36B will be sealed off when the SIMV switch 20 is in the ON position. Accordingly, the bellows device 18B will move slowly, in proportion to the setting of the adjustable restrictor 26. For example, the restrictor 26 may be set to provide for a complete stroke of the bellows device 18B over a period of four exhalation half-cycles. However, when the stroke of the exhalation time is completed the stroke sensor 18C provides a signal at the port 24B, and also switches the SIMV flip flop 50 so that its output 50A to the capacitive device 28A is terminated. However, the diaphragm 24A will maintain the ports 24A and 24B in a sealed condition until the capacitive device 28A discharges through the OR/NOR circuit 46 for a predetermined time period. When the capacitive device 28A discharges sufficiently to unseal the ports 24A and 24B the signal from the stroke sensor is coupled as an input to the master flip flop 10 causing it to provide an inspiratory command. Also, during such period since no output signals are received by the OR/NOR circuit 46 that circuit provides a signal at its NOR output which is used to close the exhalation valve.

Thus, in summary, in the operation of the embodiment illustrated in FIG. 2, when the apparatus is operating in its assist/control mode, and when the SIMV switch 20 is in its OFF position, the patient's breathing cycles are controlled by means of the master flip flop 10 which is operated in accordance with a predetermined inhale/exhale ratio dependent upon the inspiration and exhalation timers 44 and 18; and, the apparatus may assist the patients breathing in response to voluntary breaths by the patient by means of the patient trigger circuit 14 which will cause the master flip flop 10 to generate an inspiration signal prior to the timing-out of the exhalation timer. In any event, during such mode of operation the exhalation valve is maintained in a closed position during the inspiration half-cycles, so that the patient receives a mandatory breath during each half-cycle. When it is desired to wean the patient from the apparatus, the SIMV switch is placed in its ON position so that the timing period for the exhalation timer 18 is extended. The patient is then permitted to voluntarily initiate his breathing cycle by means of the patient trigger circuit 14, but the exhalation valve is left open so that the patient may voluntarily exhale even during the inspiration half-cycle. However, when the extended timing period for the timer 18 terminates, and when the patient initiates his next inspiratory period, the exhalation valve is closed so that the patient must accept a full supply of oxygen during the inspiration period. On the other hand, if the patient does not initiate an inspiratory half-cycle after termination of the extended SIMV exhalation timing period, such cycle will be automatically initiated four seconds later.

Accordingly, during the SIMV mode the patient is permitted to breath voluntarily, but at intermittent periods, determined by the setting of the restrictor 26, a mandatory breath is supplied to the patient, such mandatory breath being synchronized with the patient's voluntary breathing.

Figure 3:
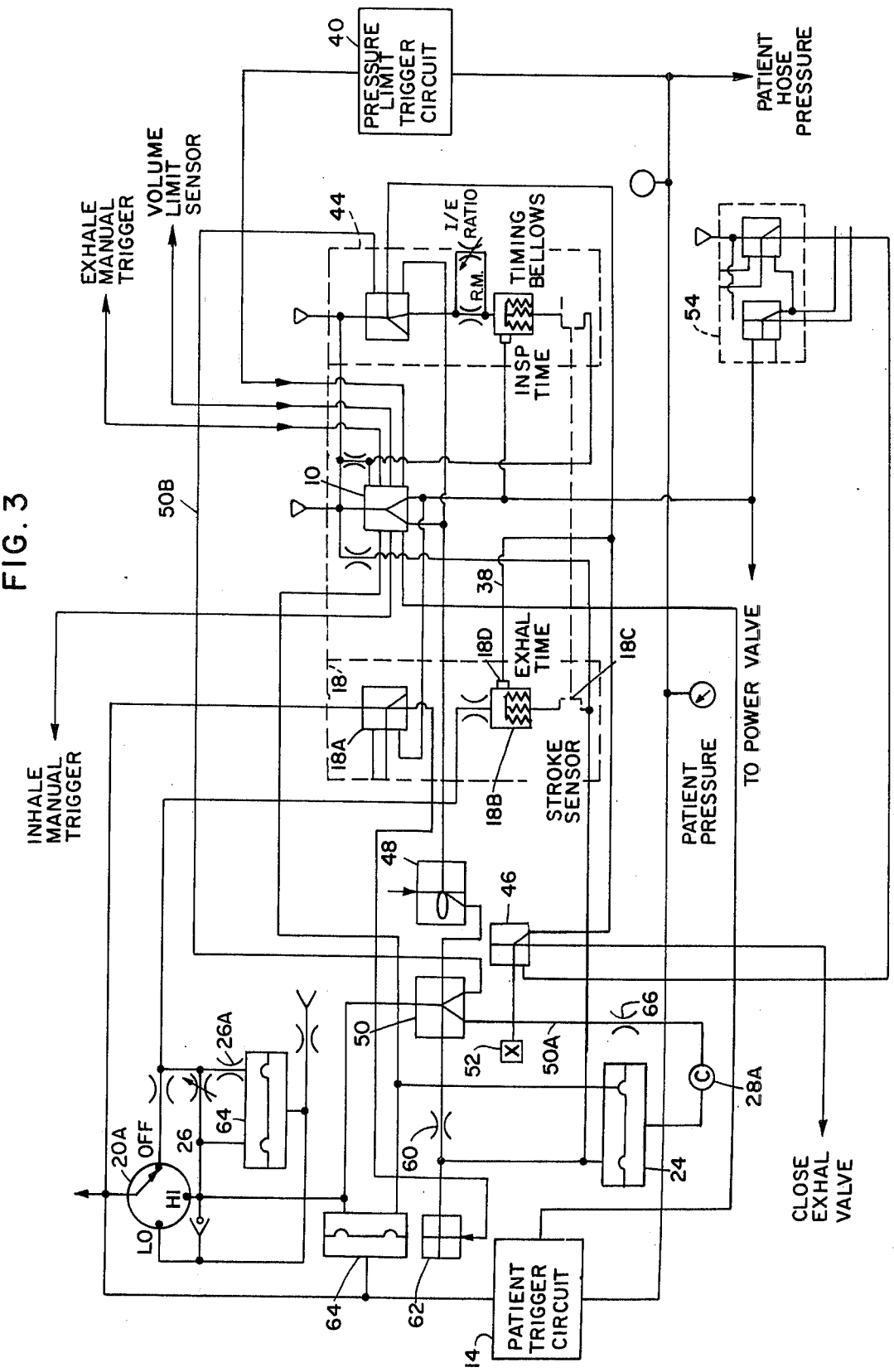
FIG. 3 is a circuit diagram illustrating a modification of the embodiment of FIG. 1.

Referring now to FIG. 3 of the drawings, a modification of the above-discussed SIMV circuitry is illustrated wherein two ranges of intermittent periods for mandatory breaths are provided. In the embodiment shown in FIG. 3 an OR circuit 48, a flip flop circuit 50, an OR/NOR circuit 46, a capacitive device 28A, and a switch 24, all operate in essentially the same manner as in the embodiment shown in FIG. 2. In this regard, the flip flop 50 is deenergized whenever the switch 20A is in the OFF position, so that the SIMV circuitry does not function, and so that the patient's breathing is then controlled by the exhalation and inspiration timers according to the specific inhale/exhale ratio determined thereby. Again, when the switch 20A is in the OFF position the patient's voluntary breathing may be merely assisted by the circuitry. Thus, his attempts to inhale may trigger an inspiration half-cycle in response to an output from the patient trigger circuit 14, but the exhalation valve is maintained in a closed position during inspiration periods so that the patient is forced to accept full volumes of oxygen during such period.

When the patient's ability to breath voluntarily has progressed to a point where it is desired to wean him from dependence on the apparatus, the selector switch 20A is positioned in a HI SIMV mode wherein the timing period for the exhalation timer is extended by supplying air thereto through the variable restrictor 26, and through a fixed restrictor 26A connected in parallel therewith through a diaphragm switch 56. The parameters of the restrictors 26, 26A may be selected to permit, for example, a range of 4 to 16 mandatory breaths per minute. When the patient's ability to breath voluntarily progresses further, the selector switch 20A may be positioned to provide a L0 SIMV mode wherein the diaphragm switch 56 blocks the parallel path through the restrictor 26A so that air is supplied to the exhalation timer solely through the variable restrictor 26, to further increase the timing period for the exhalation timer 18. In this regard, the characteristics of the restrictor 26 may permit a mandatory breath rate of 0.3–5 breaths per minute. In the L0 SIMV mode, air is coupled to the restrictor 26 through a diode 58 which is connected across the HI and L0 SIMV contacts of the switch 20A. Again, as is evident from FIG. 3, the flip flop 50 is activated only when one of the SIMV modes has been selected, and an output is applied to the flip flop 50 from the OR circuit 48 at the commencement of each exhalation cycle by means of a conduit coupled to the exhale command output 12A of the flip flop 10. Thus, as in the embodiment illustrated in FIG. 2, when one of the SIMV modes is selected the patient may voluntarily initiate each inspiration cycle by means of the trigger circuit 14, and the exhalation valve is left open during the inspiration half-cycle and during the timing period of the exhalation timer, so that the patient may voluntarily exhale. At the completion of the timing period of the exhalation timer 18, its sensor 18C provides an output coupled to the SIMV flip flop 40 which terminates its supply to the capacitive device 28A so that that device begins to discharge. If the patient voluntarily initiates an inspiration half-cycle while the capacitive device is discharging, the exhalation valve is closed by the OR/NOR circuit 46 so that the patient is forced to accept a mandatory breath. If, however, the patient does not voluntarily initiate an inspiration half-cycle, during a period of four seconds after generation of the signal by the sensor 18C, the capacitive device 28A will have discharged sufficiently to cause the switch 24 to provide a short circuit between the sensor signal and an input to the main flip flop 10, to automatically initiate an inspiration half-cycle.

In the embodiment of FIG. 3, the supply of air to the exhalation timer bellows 18B is coupled directly from the output circuitry connected to a selector switch 20A so that the timing bellows is continuously charged with air as distinguished from the embodiment illustrated in FIG. 2 wherein air is supplied through the NOR circuit 18A to the bellows 18B only during the exhalation half-cycles. Accordingly, in the embodiment of FIG. 3 the timing period of the exhalation timer can be more accurately controlled, since it does not depend in any way upon the duration of the inspiration half-cycles.

The continuous supply of air to the exhalation timer 18 in the embodiment of FIG. 3, while it increases the accuracy of the frequency of mandatory intermittent breaths, gives rise to the possibility that the exhalation timer 18 will time-out during an inspiration half-cycle, and if the patient's voluntary breathing is relatively slow, the four second delay provided by the capacitive device 28A may terminate. To prevent the SIMV circuitry from attempting to initiate a mandatory inspiration half-cycle while a voluntary inspiration half-cycle is in progress, a restrictor 60 is provided in the circuit between the sensor 18C and the input to the flip flop 50, so that the sensor signal will be insufficient to trigger the flip flop 50. Then, an amplifier device 62 has its output connected to the sensor signal conduit to supply sufficient air through the restrictor 60 to trigger the flip flop 50 only when the main flip flop is in an exhalation mode. This function is accomplished by connecting the output of the NOR circuit 18A to the input of the amplifier 62.

An additional diaphragm switch 64 is incorporated in the embodiment illustrated in FIG. 3 to preclude any inadvertent operation of the SIMV circuitry when the primary mode selector is in any position other than the assist-control mode. In this regard, a connection is made through the communicating ports of the diaphragm switch 64, from the supply input to the flip flop 50 to an inspiration trigger input to the main flip flop 10. The communicating ports of the diaphragm switch 64 are sealed off at all times during the assist-control mode, but will drive the main flip flop 10 into a continuous inspiration cycle if a signal is detected at the supply input to the flip flop 50 during modes other than the assist-control mode. Such continuous inspiration will generate an alarm signal in the apparatus to indicate its malfunction.

During the operation of the circuitry in the SIMV mode, when the frequency of breathing exceeds 12 breaths per minute, the four second time delay provided by the capacitive device 28A will be excessive. This problem is alleviated by providing a restrictor 66 in the supply conduit 50A from the flip flop 50, in order to increase the charging time for the capacitive device 28A as a result of this increased charging time, the capacitive device 28A will not fully charge during high breathing-rate cycles, so that the four second delay period caused by the capacitive device 28A will be decreased.

Various modifications of the circuitry disclosed herein will be apparent to those skilled in the art, wherefore it is stressed that the scope of this invention is not limited to the disclosed circuitry, but includes all modification thereof encompassed by the following claims.

I claim:

1. In a patient ventilator including a device for supplying air to a patient through a ventilating hose, a conduit through which the patient may exhale, and circuitry for controlling the breathing of a patient and for assisting the voluntary breathing of a patient, an improvement comprising:

means for initiating an inspiration half-cycle of a breathing period during which air is supplied to a patient through a ventilating hose; means for initiating an exhalation half-cycle of a breathing period during which the patient may exhale through a conduit; a patient trigger circuit means for sensing an inhalation attempt by the patient, said patient trigger circuit having an output coupled to actuate said inspiration initiating means; timer means having an output for providing a trigger signal at the end of a predetermined period; delay circuit means coupled between said timer means output and an input to said inspiration initiating means for actuating the latter, unless previously actuated by said patient trigger means, after a delay period responsive to said timer means trigger signal; means for selectively opening and closing the exhalation conduit; and control circuit means having an input coupled to said timer means output, having a first output coupled to actuate said conduit opening and closing means for closing said conduit during inspiration half-cycles initiated immediately subsequent to the generation of trigger signals by said timer means, and for opening said conduit during all other portions of said breathing periods, and said control circuit means having a second output coupled to said timer means for resetting said timer means when said immediately subsequent inspiratory half-cycles are initiated, wherein the patient's voluntary breathing is interrupted intermittently in response to said predetermined timing period, whereafter a mandatory inspiration half-cycle is applied as a result of the said closing of the exhalation conduit, said mandatory inspiration half-cycle being synchronized with the patient's voluntary inhalation in response to said patient trigger means.

2. A patient ventilator as set forth in claim 1, wherein said delay circuit comprises capacitive means coupled to said control circuit means for being actuated to receive a charge of air during said predetermined timing period, and a diaphragm switch having a sealed chamber provided with first and second ports coupled respectively to said timer means output and said inspiration initiating means, said switch having a diaphragm for sealing said first and second ports while said capacitive means is charged, and for permitting communication between said ports when said capacitive means discharges after said delay period.

3. A patient ventilator as set forth in claim 1, further comprising a selector switch having a selector contact, and means coupled between said selector switch contact and said timer means to decrease said predetermined period of said timer means, said selector switch contact being coupled to said control circuit means for energizing the latter to selectively control said conduit opening and closing means to close said conduit during every inspiration half-cycle.

4. A patient ventilator as set forth in claim 1, further comprising a selector switch having a selector contact, and means coupled between said selector contact and said timer means for increasing said predetermined period of said timer means, to thereby decrease the frequency of said mandatory inspiration half-cycle.

* * * * *